US00PP16239P2

(12) United States Plant Patent
Mak

(10) Patent No.: US PP16,239 P2
(45) Date of Patent: Feb. 7, 2006

(54) LILY PLANT NAMED 'TINY HOPE'

(50) Latin Name: *Lilium hybrida*
Varietal Denomination: Tiny Hope

(75) Inventor: Nicolaas Aloysius Maria Mak, 't Zand (NL)

(73) Assignee: Mak 't Zand B.V., 't Zand (NL)

( * ) Notice: Subject to any disclaimer, the term of this patent is extended or adjusted under 35 U.S.C. 154(b) by 46 days.

(21) Appl. No.: 10/973,057

(22) Filed: Oct. 23, 2004

(51) Int. Cl.
*A01H 5/00* (2006.01)

(52) U.S. Cl. ..... Plt./314

(58) Field of Classification Search ..... Plt./314
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Asiatic Hybrid Lily plant named 'Tiny Hope' characterized by its medium to large plant size; vigorous growth habit; freely flowering habit; dark red-colored tepals that are slightly recurved and ruffled at the apex; and good postproduction longevity.

1 Drawing Sheet

Botanical classification/cultivar designation: *Lilium hybrida* cultivar Tiny Hope.

BACKGROUND OF THE INVENTION

The present Invention relates to a new and distinct cultivar of Asiatic Hybrid Lily plant, botanically known as *Lilium hybrida,* and hereinafter referred to by the name 'Tiny Hope'.

The new Asiatic Hybrid Lily is a product of a planned breeding program conducted by the Inventor in 't Zand, The Netherlands. The objective of the breeding program was to develop new potted Asiatic Hybrid Lily plants with erect flowers, attractive flower coloration and good postproduction longevity.

The new Asiatic Hybrid Lily originated from a cross-pollination in 1995 of an unnamed proprietary Asiatic Hybrid Lily, not patented, as the female, or seed, parent with an unnamed proprietary Asiatic Hybrid Lily, not patented, as the male, or pollen, parent. The cultivar Tiny Hope was discovered and selected by the Inventor as a flowering plant within the resultant progeny of the cross-pollination in a controlled environment in 't Zand, The Netherlands in May, 1998.

Asexual reproduction of the new Asiatic Hybrid Lily by bulb scales in a controlled environment in 't Zand, The Netherlands since November, 1998, has shown that the unique features of this new Asiatic Hybrid Lily are stable and reproduced true to type in successive generations.

SUMMARY OF THE INVENTION

The cultivar 'Tiny Hope' has not been observed under all possible environmental conditions. The phenotype may vary somewhat with variations in environment such as temperature and light intensity without, however, any variance in genotype.

The following traits have been repeatedly observed and are determined to be the unique characteristics of 'Tiny Hope'. These characteristics in combination distinguish 'Tiny Hope' as a new and distinct cultivar of Asiatic Hybrid Lily:

1. Medium to large plant size; vigorous growth habit.
2. Freely flowering habit.
3. Dark red-colored tepals that are slightly recurved.
4. Good postproduction longevity.

Plants of the new Asiatic Hybrid Lily differ from plants of the parent selections primarily in tepal coloration as plants of the female parent have red-colored tepals and plants of the male parent have orange-colored tepals.

Plants of the new Asiatic Hybrid Lily can be compared to plants of the Asiatic Hybrid Lily cultivar Crimson Pixie, disclosed in U.S. Plant Pat. No. 6,557. In side-by-side comparisons conducted in 't Zand, The Netherlands, plants of the new Asiatic Hybrid Lily differed from plants of the cultivar Crimson Pixie, in the following characteristics:

1. Plants of the new Asiatic Hybrid Lily were taller than plants of the cultivar Crimson Pixie.
2. Plants of the new Asiatic Hybrid Lily had smaller leaves than plants of the cultivar Crimson Pixie.
3. Plants of the new Asiatic Hybrid Lily were more freely flowering than plants of the cultivar Crimson Pixie.
4. Plants of the new Asiatic Hybrid Lily had larger flowers than plants of the cultivar Crimson Pixie.
5. Plants of the new Asiatic Hybrid Lily and the cultivar Crimson Pixie differed in flower coloration.

DESCRIPTION OF THE PHOTOGRAPH

The accompanying colored photograph illustrates the overall appearance of the new Asiatic Hybrid Lily, showing the colors as true as it is reasonably possible to obtain in colored reproductions of this type. Colors in the photograph may differ slightly from the color values cited in the detailed botanical description which accurately describe the colors of the new Asiatic Hybrid Lily. The photograph comprises a side perspective view of a typical flowering plant of 'Tiny Hope' grown in a container.

DETAILED BOTANICAL DESCRIPTION

In the following description, color references are made to The Royal Horticultural Society Colour Chart, 2001 Edition, except where general terms of ordinary dictionary significance are used. The aforementioned photograph and following observations and measurements describe plants that had been growing for about 70 days in 't Zand, The Netherlands under commercial practice in a glass-covered greenhouse. Plants were grown at a minimum temperature of about 15° C. and the average daylength was about 14 hours. Measurements and numerical values represent averages for typical flowering plants. The photograph and the description were taken during the late spring.

Botanical classification: *Lilium hybrida* cultivar Tiny Hope.

Parentage:

*Female, or seed, parent.*—Unnamed proprietary selection of *Lilium hybrida,* not patented.

*Male, or pollen, parent.*—Unnamed proprietary selection of *Lilium hybrida,* not patented.

Plant description:

*Plant form/growth habit.*—Upright flowering plant; single erect flowering stem with a terminal cluster of flowers. Medium to large plant size. Vigorous growth habit.

*Plant height, soil level to top of flowers.*—About 50 cm.

*Plant diameter.*—About 16 cm.

*Flowering stems.*—Internode length: About 6 to 9 mm. Texture: Smooth, glabrous. Color: 146B.

*Leaves.*—Arrangement: Alternate; simple; sessile. Quantity of leaves per plant: About 40. Length, lower leaves: About 4 cm. Width, lower leaves: About 1.2 cm. Length, upper leaves: About 6.2 cm. Width, upper leaves: About 1.8 cm. Shape: Lanceolate. Apex: Acute. Margin: Entire. Texture, upper and lower surfaces: Glabrous, smooth; leathery. Venation pattern: Parallel. Color: Developing and fully expanded leaves, upper surface: 141A. Developing and fully expanded leaves, lower surface: 146B. Venation, upper and lower surfaces: Similar to lamina.

*Bulbs.*—Diameter: About 14 to 16 cm. Texture: Smooth. Color: Close to 155D.

Flower description:

*Flowering habit.*—Terminal single flowers arranged on a raceme on long, mostly erect and strong flowering stems. Flowers slightly fragrant; tepals not persistent; gynoecium persistent. Flowers face mostly upright.

*Natural flowering season.*—Plants flower in June in The Netherlands. Plants can be flowered year-round in the greenhouse and forced to bloom about 65 to 70 days after planting bulbs.

*Flower longevity on the plant.*—About 10 to 14 days.

*Flower buds.*—Length: About 9 cm. Diameter: About 1.8 cm. Circumference: About 5.5 cm. Shape: Lanceolate. Texture: Smooth, glabrous. Color: 46A; towards the apex, greenish shading.

*Flowers.*—Quantity of flowers per flowering stem: Freely flowering; about seven to nine. Shape: Funnel-shaped. When fully opened, flowers flatten and reflex slightly. Diameter: About 18 cm. Depth (height): About 3 cm.

*Perianth.*—Quantity/arrangement: Six tepals per flower; imbricate. Tepal length, inner tepals: About 10 cm. Tepal length, outer tepals: About 11 cm. Tepal width, inner tepals: About 4 cm. Tepal width, outer tepals: About 3 cm. Tepal shape: Lanceolate. Tepal apex: Acute. Tepal margin: Entire. Tepal texture, upper and lower surfaces: Smooth, glabrous; leathery. Tepal color: When opening, upper surface: 46A; spots towards the base, 187A. When opening, lower surface: 42A. Fully opened, upper surface: 46A; spots towards the base, 187A; midrib, 35C; venation, 35C. Fully opened, lower surface: 42A.

*Pedicels.*—Angle: About 45° from vertical. Strength: Strong. Length: About 3.5 to 4.5 cm. Diameter: About 4 mm. Texture: Smooth, glabrous. Color: 146A.

*Reproductive organs.*—Stamens: Quantity per flower: Six. Filament length: About 5.4 cm. Filament color: 35B. Anther length: About 1 cm. Anther color: 169A. Pollen color: 28B. Pistils: Quantity per flower: One. Style length: About 4 cm. Style color: 44C. Stigma color: 187A.

*Fruits/seeds.*—Fruit and seed development has not been observed.

Disease/pest resistance: Some resistance to Botrytis and Pythium has been observed on plants of the new Asiatic Hybrid Lily. Resistance to pest and other pathogens common to Asiatic Hybrid Lilies has not been determined.

It is claimed:

1. A new and distinct cultivar of Lily plant named 'Tiny Hope', as illustrated and described.

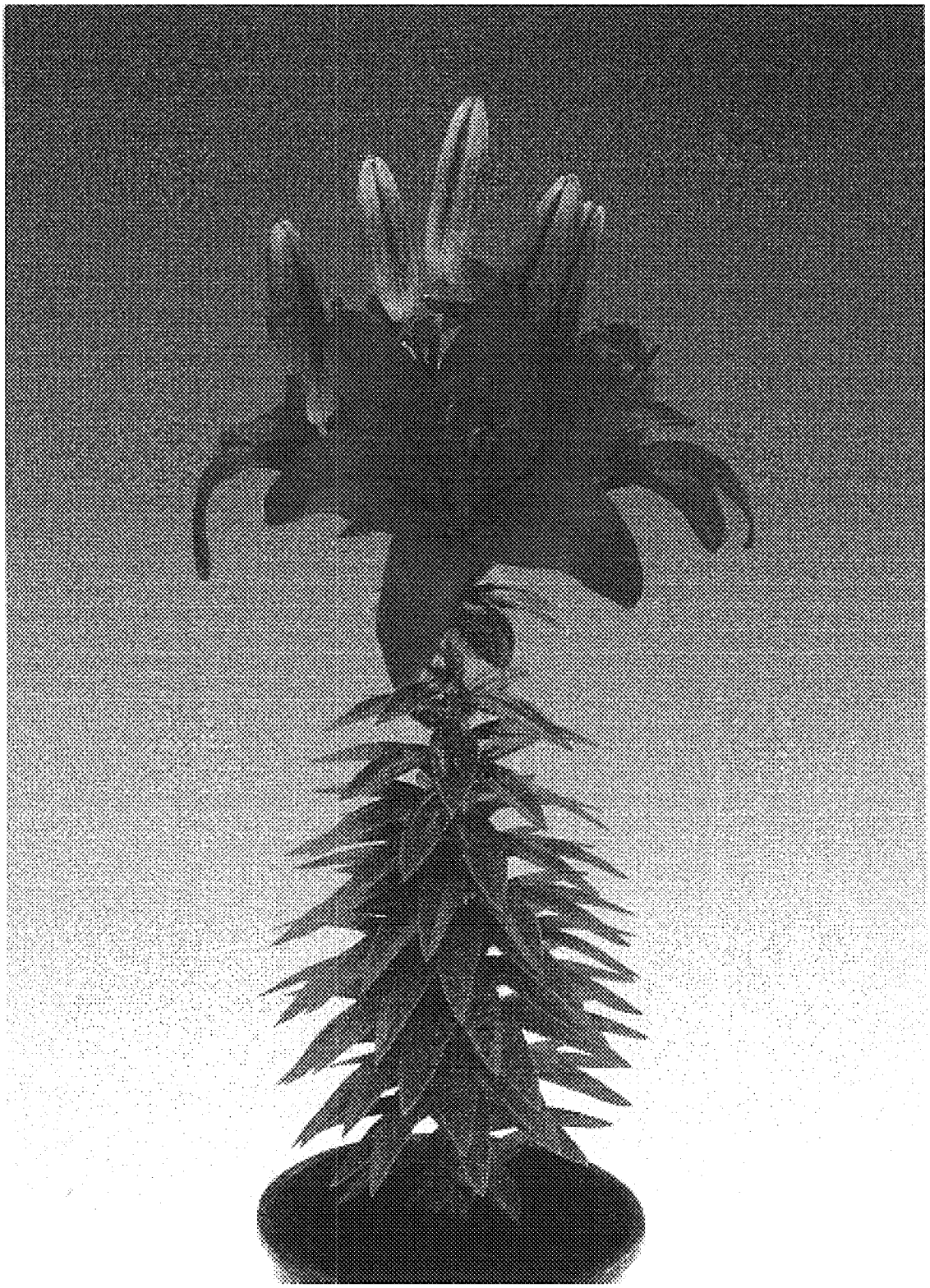

* * * * *